United States Patent
Pathak et al.

(10) Patent No.: US 10,793,539 B2
(45) Date of Patent: Oct. 6, 2020

(54) PROCESS FOR THE PREPARATION OF TOCOLS AND SQUALENE

(71) Applicant: PRAJ INDUSTRIES LIMITED, Pune (IN)

(72) Inventors: Pallavi Vinitkumar Pathak, Pune (IN); Prajakt Subhash Charhate, Pune (IN); Mangesh Ganesh Kurkarni, Pune (IN)

(73) Assignee: PRAJ INDUSTRIES LIMITED, Pune (IN)

( * ) Notice: Subject to any disclaimer, the term of this patent is extended or adjusted under 35 U.S.C. 154(b) by 0 days.

(21) Appl. No.: 16/466,843

(22) PCT Filed: Nov. 27, 2017

(86) PCT No.: PCT/IN2017/050557
§ 371 (c)(1),
(2) Date: Jun. 5, 2019

(87) PCT Pub. No.: WO2018/109780
PCT Pub. Date: Jun. 21, 2018

(65) Prior Publication Data
US 2019/0345127 A1   Nov. 14, 2019

(30) Foreign Application Priority Data

Dec. 16, 2016 (IN) .............................. 201621042970

(51) Int. Cl.
*C07D 311/72* (2006.01)
*C07C 11/21* (2006.01)

(52) U.S. Cl.
CPC ............ *C07D 311/72* (2013.01); *C07C 11/21* (2013.01)

(58) Field of Classification Search
CPC .................................................... C07D 311/72
USPC ............................................................ 549/72
See application file for complete search history.

(56) References Cited

U.S. PATENT DOCUMENTS

| | | | | |
|---|---|---|---|---|
| 5,190,618 A | * | 3/1993 | Top ...................... | C07D 311/72 159/49 |
| 6,656,358 B2 | * | 12/2003 | May ..................... | B01D 15/265 210/634 |
| 7,161,055 B2 | * | 1/2007 | Choo ..................... | C11B 3/001 549/410 |
| 7,544,822 B2 | * | 6/2009 | Ho ........................ | C07C 403/24 549/413 |

FOREIGN PATENT DOCUMENTS

| | | | | |
|---|---|---|---|---|
| EP | 033472 | * | 3/1989 | ......... C07D 311/172 |
| EP | 0333472 A2 | | 9/1989 | |
| EP | 1689353 B1 | | 1/2013 | |

OTHER PUBLICATIONS

International Search Report and Written Opinion for PCT/IN2017/050557, dated Feb. 20, 2018.

* cited by examiner

*Primary Examiner* — Nizal S Chandrakumar
(74) *Attorney, Agent, or Firm* — Lisbeth C. Robinson; Billion & Armitage

(57) ABSTRACT

The invention relates to a process for the preparation of tocols [tocopherols (T) and tocotrienols (T3)] and squalene from vegetable oil refining by-products like fatty acid distillates. It particularly relates to the process of preparation of tocopherols, tocotrienols and squalene without any degradation from the fatty acid distillates obtained during processing of oils from the palm.

5 Claims, No Drawings

PROCESS FOR THE PREPARATION OF TOCOLS AND SQUALENE

FIELD OF INVENTION

The invention relates to a process for the preparation of tocols [tocopherols (T) and tocotrienols (T₃)] and squalene from vegetable oil refining by-products like fatty acid distillates. It particularly relates to the process of preparation of tocopherols, tocotrienols and squalene without any degradation from the fatty acid distillates obtained during processing of oils from the palm.

BACKGROUND

Tocopherols and tocotrienols, collectively known as tocols, are phenolic compounds. They have received much attention due to their antioxidant and anticancer properties and they are widely used in pharmaceuticals as supplements, nutraceuticals as well as in fine chemicals. Squalene, which is widely found in the shark liver oil, is also present in palm oil and it is a valuable constituent in cosmetics as well as in food supplements.

Crude palm oil [CPO] contains about 1% by weight minor components which include carotenes, tocols in the form of tocopherols and tocotrienols and hydrocarbons such as squalene and phytosterols. Crude palm oil is usually refined by steam distillation. In the steam distillation process, the palm oil, containing mainly triglycerides, is separated from free fatty acids [FFA] and other volatile compounds. The volatile fraction that is obtained in this process is known as palm fatty acid distillate [PFAD]. Palm fatty acid distillate typically contains not only free fatty acids but also monoglycerides, diglycerides and other valuable materials including tocotrienols, ($\alpha$-, $\beta$-, $\gamma$-, and $\delta$-), tocopherols ($\alpha$-, $\beta$-, $\gamma$-, and $\delta$-), sterols and squalene.

Tocols are an important group of organic molecules widely used in pharmaceutical and nutraceutical products. Many vegetative plant materials like roots, stems, leaves or seeds produce and store the tocols. The natural tocols have been widely used in the preparations like cosmetic products, animal and human healthcare products. The tocopherols [vitamin E derivatives] of plant origin are widely used as vitamin supplements in various food and cosmetics products. Besides, they are also used as raw materials for the preparation of several intermediate chemicals or derivatives of unique properties for the preparation of several medicinal molecules.

The tocotrienols exhibit more powerful antioxidant and anti cancer power than the tocopherols. This makes palm oil special as it is the richest sources of natural tocotrienols. Palm tocols is also useful to lower the cholesterol level in the body. Squalene is used to boost the immunes system. In pharmaceutical industry, squalene is widely used in the formulation of pharmaceutical creams and lotions.

The tocols and squalene are present in large amounts in oil seeds of several types. During extraction and refining of oils, tocols and squalene containing fractions are separated and further processed to isolate the tocols and squalene as by-products of higher values. Several methods have been known that separate these components. However, the quality of the final tocols and squalene preparations largely depends on the physical and chemical processes used to isolate it.

The major issues with the recovery of tocols and other byproducts from materials like PFAD are the yield and quality of the final compositions. They form raw materials for the preparation of many derivatives used in pharmaceutical preparations. Thus, there is still a need for a process to produce tocols and squalene from plant materials using green, non-toxic and economic methods with higher quality of the final preparations for use in specialty applications like pharmaceutical and nutritional products.

The invention involves a process for producing a product that is enriched in tocols and other components of palm oil such as squalene. The process is simple and effective achieving desired results. The product of the invention is a material that has a high commercial value and can be used in a number of different applications.

DETAILED DESCRIPTION OF THE INVENTION

In one embodiment of the invention, the process comprises providing a fatty acid distillate obtained from palm oil having free fatty acids and tocols with other compounds; subjecting said distillate to esterification with a methanol in the presence of an acid catalyst at desired temperature and pressure for desired time, and allowed to form a crude fatty acid methyl ester and tocols mixture as an esterified stream. Said esterified stream is then subjected to three molecular distillation steps forming an enriched tocols and squalene fraction. Said tocols and squalene fraction is subjected to chromatographic separation to get final tocols and squalene preparation of higher yield and purity. Said squalene fraction can be further purified to get about 99% pure squalene products. The tocol fractions are useful for the preparation of pharmaceutical, nutraceutical or cosmetic products. It may be appreciate that the steps disclosed herein are equally applicable to a fatty acid distillate other than herein described as primary components of different distillates are similar.

In another embodiment of the invention, the process to enrich tocols and squalene comprises five steps namely: 1] esterification of palm fatty acid distillate 2] first molecular distillation of mixture 3] second molecular distillation of first residue stream 4] final molecular distillation of second distillate stream and 5] chromatographic separation of final residue stream. Each step has one or more elements for performing specific or optional functions as required for removing between about 85% to about 95% free fatty acids and achieving enrichment of tocopherols, tocotrienols and squalene from the raw material. A person skilled in the art may appreciate different variations and/or combinations of these elements that may be used to perform the objects of the invention disclosed herein.

Step 1: Esterification of PFAD

The palm fatty acid distillate [PFAD] containing tocols of about 1% by weight and squalene about 2.5% by weight along with free fatty acids, sterols and glycerides is subjected to esterification in the presence of an acid catalyst of about 0.5% to about 4% with an alcohol like methanol or ethanol at a temperature of about 60° C. to about 13° C., under nitrogen pressure of about 10 kg/cm² for about 4 h. During this process the free fatty acids are converted into esters. Then said reaction mass is cooled gradually to room temperature, methanol is recovered by distillation. Obtained esterified stream having fatty acid methyl esters along with tocols & squalene mixture is further washed with water to remove the catalyst. Then said esterified stream is dried to remove any traces of moisture in it.

Step 2: First Molecular Distillation of Esterified Stream

In this step, said esterified stream of step 1 is subjected to a first molecular distillation step at the temperature between about 135° C. to about 190° C. in vacuum of between about 0.01 mmHg to about 0.40 mmHg at a feed flow rate between about 25 kg/h to about 35 kg/h and agitation rate of about 280 RPM for removing remaining fatty acid methyl ester and to enrich tocols and squalene in it. A residue stream [the first residue stream] comprised about 2% to about 4% tocols by weight and about 4% to about 8% squalene.

Step 3: Second Molecular Distillation of First Residue Stream

The first residue stream obtained is further subjected to a second molecular distillation step at a temperature between about 200° C. to about 250° C. in vacuum of between about 0.01 mmHg to about 0.20 mmHg at a feed flow rate of between about 10 kg/h to about 20 kg/h and agitation rate of about 280 RPM. The second molecular distillation step is performed to distil most of the tocols & squalene in distillate and to remove high boilers in the second residue stream. Said distillation gives a distillate stream which comprises about 5% to about 10% by weight of tocols, where as the squalene concentration is about 9% to about 13% by weight.

Step 4: Final Molecular Distillation of Second Distillate Stream

The second distillate stream obtained in step 3 is further subjected to a final molecular distillation step at a temperature between about 140° C. to about 180° C. in vacuum of between about 0.02 mmHg to about 0.40 mmHg at a feed flow rate of between about 25 kg/h to about 35 kg/h and agitation rate of about 280 RPM for removing final traces of fatty acid methyl ester from the distillate. Said distillation gives a final residue stream which comprises about 7% to about 12% tocols by weight and about 10% to about 15% squalene by weight. Said residue stream is processed further to enrich tocols and squalene to desired purity and quality in final step by chromatography.

Step 5: Chromatographic Separation of Final Residue Stream

The final residue stream obtained in step 4 is further subjected to chromatographic separation to separate tocols and squalene from fatty acids, fatty acid methyl esters and glycerides present in the residue. The final residue stream obtained in step 4 is loaded to the silica column having a mesh size of 60-120 mesh for about 55 minutes. Next, the column is eluted with a mixture of hexane & ethyl acetate. The amount of ethyl acetate in the solution varies from 1% to 100%. First about 2% ethyl acetate containing hexane is passed, next about 5% ethyl acetate containing hexane is passed, then about 10% ethyl acetate containing hexane is passed, followed by about 100% ethyl acetate to remove all the polar impurities. At last column is regenerated by using hexane. First fraction of solvent is collected & solvent is distilled off so that first fraction which majorly contains about 45% to about 60% squalene is separated. The second cut of solvent which consist of tocols fraction is further collected and solvent is distilled off to collect second fraction containing about 15% to about 30% tocols. And further final fraction of solvent which mainly contain highly polar impurities such as FFA is obtained after evaporation of solvent which also contain less fraction of tocols in it.

In yet another embodiment, for chromatography the feed and solvent ratio used for elution is about 1:60 for the first column and about 1:55 for the subsequent columns. The bulk density of silica used for chromatography is between about 0.50 to 0.66 g/cm$^3$ for getting up to 20% tocols and 50% squalene purity.

In another embodiment of the invention, process of preparation of tocols and squalene is initiated with first step of esterification. It is used to convert free fatty acids into esters. First molecular distillation step is used to remove fatty acid methyl esters. Second molecular distillation step is used to remove high boilers and final molecular distillation is used to remove traces of fatty acid methyl esters and to concentrate tocols and squalene in the residue. The column chromatography step is used to concentrate and purify the tocols and squalene. Where column chromatography is used the process afforded 18% to 25% tocols along with 45%-60% squalene by weight.

This invention discloses a process for the preparation of tocols and squalene from palm fatty acid distillate as value added by-products of oil refining industry. The process having several advantages over the known methods as:

1. The three part molecular distillation route is a simple and cost effective process.
2. The final concentration of tocols obtained is about 18% to 25% by weight using a chromatographic separation step.
3. The final concentration of squalene obtained is about 45% to 60% by weight.
4. The disclosed process significantly reduces solvents used, significantly saving in the utilities and solvents.
5. Fatty acid methyl esters (about 75% to 85% by weight) are by-product of commercial value.
6. Solvents are recycled in the process after recovery with minimum loss.
7. The column chromatography step gives up to 25% tocols purity by weight along with up to 95% recovery of the product.
8. The column chromatography step gives up to 60% squalene purity by weight along with up to 95% recovery of the product.
9. Stationary phase of column chromatography may be used up to 60 times without loss of efficiency.

EXAMPLES

Examples provided below give wider utility of the invention without any limitations as to the variations that may be appreciated by a person skilled in the art. A non-limiting summary of various experimental results is given in the examples and tables, which demonstrate the advantageous and novel aspects of the process for preparation of tocols and squalene from a fatty acid distillate.

The characteristics of the suitable starting materials required for the above described process for producing the desired final tocopherol preparations are summarized in TABLE 1.

TABLE 1

Specifications of PFAD that may be used to prepare the tocols & squalene.

| Parameters | Units | PFAD {Approx.} |
| --- | --- | --- |
| Free Sterol | % w/w | 0.3 |
| Acid value | mg KOH/gm | 151 |
| Tocopherol | % w/w | 0.4 |
| Tocotrienol | % w/w | 0.7 |
| Squalene | % w/w | 2 |
| Sap value | — | 180 |
| Unsap matter | % w/w | 3.5 |
| Iodine value | — | 79 |

Example 1

About 100 kg of PFAD [containing about 0.4% of tocopherols, 0.74% of tocotrienol, about 2.14% of squalene and 76% of free fatty acids by weight] was reacted with about 30 kg of methanol in the presence of 2 kg of methane sulphonic acid [MSA] at temperature of about 60° C., under nitrogen pressure of about 10 kg/cm$^2$ for about 4 h. Then said reaction mass was gradually cooled to room temperature and methanol was recovered by distillation. Obtained fatty acid methyl esters and tocols mixture was further washed with water to remove the catalyst. Then the mixture was dried to remove any traces of moisture in it. Next, said mixture was subjected to molecular distillation step 1 to remove fatty acid methyl esters from the mixture at temperature of about 140° C. and vacuum of about 0.05 mmHg, at a flow rate of about 30 kg/h and at agitation of about 280 RPM to enrich tocopherols in the residue. This step afforded about 30.5 kg of first residue stream containing about 1.16% of tocopherols, 2.09% of tocotrienol and 6.15% of squalene by weight. Next, said first residue stream was again passed through molecular distillation step 2 at temperature of about 235° C., at vacuum of about 0.1 mmHg, at a flow rate about 15 kg/h and at agitation of about 280 RPM. This second distillation step produced about 17.6 kg of second distillate stream with about 2.03% of tocopherols, about 3.82% of tocotrienol & about 11.01% of squalene by weight. Said second distillate stream was then subjected to molecular distillation step 3 at temperature of between about 140° C. to about 180° C., at vacuum of about 0.05 mmHg, at a flow rate about 32 kg/h and at agitation of about 280 RPM for removing any final traces of fatty acid methyl esters and to get about 11.2 kg of third residue stream with 3% of tocopherols, 5.74% of tocotrienol & 13.29% of squalene by weight.

Example 2

Next, about 225 gm of residue from molecular distillation step 3 was loaded to a column of 70 mm internal diameter and 770 mm height, filled with about 1625 gm of silica having a mesh size of between 60-120; the time taken for loading was about 55 minutes. The column was eluted with a mixture of hexane and ethyl acetate. Content of ethyl acetate in the mixture varied from 0% to 100%. First, about 1553 ml of 100% hexane was passed, followed by about 1553 ml of 2% ethyl acetate in hexane, followed by 3108 ml of 5% ethyl acetate in hexane, then about 3108 ml of 10% ethyl acetate in hexane, and finally about 1553 ml of 100% ethyl acetate to remove all the polar impurities present in the distillate. At last the column was regenerated by using 3108 ml of pure hexane. A first fraction of about 3368 ml solvent was collected and solvent is distilled off to afford about 58.25 gm of squalene in the residue having purity of about 50% by weight. The second cut of about 8000 ml of solvent was collected and solvent was distilled off to afford about 74.32 gm of second fraction containing about 25% tocols (8.69% of tocopherol and 15.97% of tocotrienol) by weight. Finally about 2610 ml of final fraction of solvent mainly with highly polar impurities such as FFA and phytosterol was obtained after evaporation of solvent. Here about 92.4 gm of FFA was obtained with about 0.46% tocols by weight.

Example 3

About 100 g of PFAD containing about 0.35% of tocopherols & 0.66% of tocotrienols, and about 2.2% of squalene by weigh; and about 151.08 mgKOH/gm of acid value was reacted with about 30 g of methanol in the presence of 2 g of methane sulphonic acid [MSA] at temperature of about 100° C. Then said reaction mass was gradually cooled to room temperature, methanol was recovered by distillation. Said reaction mass was further washed with water to remove the catalyst. Then the mixture was dried to remove any traces of moisture in it and analyzed for the recovery of tocols and squalene. After esterification about 0.35% of tocopherols & 0.3% of tocotrienol and about 1.04% of squalene by weight; and 5.28 mgKOH/gm acid value was obtained. With total recovery of tocopherols at about 100%, total recovery of tocotrienols at about 45.45% and with total recovery of squalene at about 48.59%.

Example 4

About 100 g of PFAD containing about 0.35% of tocopherols & 0.66% of tocotrienols and about 2.2% of squalene; and about 151.08 mg KOH/gm acid value was reacted with about 30 g of methanol in the presence of 2 g of methane sulphonic acid [MSA] at temperature of about 65° C. Then said reaction mass was gradually cooled to room temperature and methanol was recovered by distillation. Said reaction mass was further washed with water to remove the catalyst. Then the mixture was dried to remove any traces of moisture in it and analyzed for the recovery of tocols and squalene. After esterification about 0.32% of tocopherols & 0.52% of tocotrienol and about 1.8% of squalene; and 4.59 mg KOH/gm acid value was obtained. At the end the total recovery of tocopherol was about 91.43%, total recovery of tocotrienols was 78.79% and total recovery of squalene was 84.11%.

Example 5

About 100 g of PFAD containing about 0.32% of tocopherols & 0.66% of tocotrienols and about 2.2% of squalene; and about 150.14 mg KOH/gm acid value was reacted with about 30 g of methanol in the presence of 2 g of methane sulphonic acid [MSA] at temperature of about 65° C. under nitrogen pressure of about 2 kg/cm2 for about 4 h. Then said reaction mass was gradually cooled to room temperature, methanol was recovered by distillation. Said reaction mass was further washed with water to remove the catalyst. Then the mixture was dried to remove any traces of moisture in it and analyzed to check the recovery of tocols and squalene. After esterification, about 0.31% of tocopherols & 0.54% of tocotrienols and about 2.12% of squalene; and 4.77 mgKOH/gm acid value was obtained. The total recovery of tocopherol was 96.88%, the total recovery of tocotrienols was 81.82% and the total recovery of squalene was 96.80%.

Example 6

About 100 g of PFAD containing about 0.3% of tocopherols & 0.64% of tocotrienols and about 2.2% of squalene; and about 148.45 mgKOH/gm acid value was reacted with about 30 g of methanol in the presence of 2 g of methane sulphonic acid [MSA] at temperature of about 65° C. under nitrogen pressure of about 10 kg/cm2 for about 4 h. Then said reaction mass was gradually cooled to room temperature and methanol was recovered by distillation. Said reaction mass was further washed with water to remove the catalyst. Then the mixture was dried to remove any traces of moisture in it and analyzed to check the recovery of tocols and squalene. After esterification, about 0.3% of tocopherols & 0.58% of tocotrienol and about 2.03% squalene; and 7.1 mgKOH/gm acid value was obtained. The total recovery of tocopherols was 100%, total recovery of tocotrienols was 90.63% and total recovery of squalene was 94.85%.

We claim:

1. A process for preparation tocols and squalene comprising:
    (a) providing a fatty acid distillate comprising tocols and squalene, wherein the fatty acid distillation is obtained during the refining of palm oil and comprises up to 1% tocols by weight;
    (b) subjecting said distillate to esterification with methanol at desired conditions forming an esterified stream;
    (c) subjecting said esterified stream to a first molecular distillation at a temperature between 140° C. to 190° C. in a vacuum of between 0.010 mmHg to 0.40 mmHg at a feed flow rate between 25 kg/h to 35 kg/h and an agitation rate of 280 RPM, thereby forming a first distillate stream and a first residue stream;
    (d) subjecting said first residue stream to a second molecular distillation at a temperature between 200° C. to 250° C. in a vacuum of between 0.01 mmHg to 0.20 mmHg at a feed flow rate between 10 kg/h to 20 kg/h and an agitation rate of 280 RPM, thereby forming a second distillate stream and a second residue stream;
    (e) subjecting said second distillate stream to a final molecular distillation at a temperature between 140° C. to 180° C. in a vacuum of between 0.020 mmHg to 0.40 mmHg at a feed flow rate between 25 kg/h to 35 kg/h and an agitation rate of 280 RPM, thereby forming a final distillate stream and a final residue stream; and
    (f) subjecting said final residue stream to chromatographic separation to get a highly enriched composition of tocols and squalene, wherein said chromatographic separation is achieved using silica gel as a stationary phase.

2. The process of claim 1, wherein said first residue stream comprises 2% to 4% tocols by weight and 4% to 8% squalene by weight.

3. The process of claim 1, wherein said second distillate stream comprises 5% to 10% tocols by weight and 9% to 13% squalene by weight.

4. The process of claim 1, wherein said third residue stream comprises 7% to 12% tocopherols by weight and 10% to 15% squalene by weight.

5. The process of claim 1, wherein said chromatographic separation afforded between 15% to 30% tocols by weight and 45% to 60% squalene by weight.

* * * * *